(12) United States Patent
Okada (10) Patent No.: US 11,737,958 B2
(45) Date of Patent: *Aug. 29, 2023

(54) METHOD FOR PRODUCING UV PROTECTIVE COATING

(71) Applicant: KAO CORPORATION, Tokyo (JP)

(72) Inventor: Tomonari Okada, Yashio (JP)

(73) Assignee: KAO CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/604,685

(22) PCT Filed: Apr. 18, 2018

(86) PCT No.: PCT/JP2018/015981
§ 371 (c)(1),
(2) Date: Oct. 11, 2019

(87) PCT Pub. No.: WO2018/194087
PCT Pub. Date: Oct. 25, 2018

(65) Prior Publication Data
US 2020/0155422 A1 May 21, 2020

(30) Foreign Application Priority Data
Apr. 18, 2017 (JP) ................. 2017-082079

(51) Int. Cl.
*A61K 8/34* (2006.01)
*A61K 8/81* (2006.01)
*B05B 5/025* (2006.01)
*B05B 5/16* (2006.01)
*A61K 8/02* (2006.01)
*A61K 8/35* (2006.01)
*A61K 8/87* (2006.01)
*A61Q 17/04* (2006.01)

(52) U.S. Cl.
CPC ............. *A61K 8/027* (2013.01); *A61K 8/34* (2013.01); *A61K 8/35* (2013.01); *A61K 8/8135* (2013.01); *A61K 8/87* (2013.01); *A61Q 17/04* (2013.01); *B05B 5/0255* (2013.01); *B05B 5/1691* (2013.01); *A61K 2800/87* (2013.01); *A61K 2800/884* (2013.01)

(58) Field of Classification Search
None
See application file for complete search history.

(56) References Cited

U.S. PATENT DOCUMENTS

| | | | |
|---|---|---|---|
| 5,494,674 A | 2/1996 | Barnett et al. | |
| 6,514,504 B1 | 2/2003 | Yen et al. | |
| 6,531,142 B1 * | 3/2003 | Rabe | A61K 8/29 424/401 |
| 2002/0192252 A1 | 12/2002 | Yen et al. | |
| 2005/0002976 A1 | 1/2005 | Wu | |
| 2006/0057085 A1 * | 3/2006 | Lezer | A61K 8/29 424/63 |
| 2013/0118517 A1 * | 5/2013 | Foley | A61K 8/8182 132/200 |
| 2015/0335569 A1 | 11/2015 | Ao et al. | |
| 2015/0342855 A1 * | 12/2015 | Ao | A61K 8/29 424/78.03 |
| 2015/0342865 A1 | 12/2015 | Ao et al. | |
| 2019/0053602 A1 * | 2/2019 | Amari | A61L 26/00 |
| 2020/0121568 A1 | 4/2020 | Foley | |

FOREIGN PATENT DOCUMENTS

| | | |
|---|---|---|
| CN | 1379656 A | 11/2002 |
| CN | 1809335 A | 7/2006 |
| CN | 103492029 A | 1/2014 |
| CN | 105142604 A | 12/2015 |
| CN | 105246454 A | 1/2016 |
| CN | 108135788 A | 6/2018 |
| EP | 3 366 271 A1 | 8/2018 |
| JP | 5-262634 A | 10/1993 |
| JP | 7-258055 A | 10/1995 |
| JP | 8-259430 A | 10/1996 |
| JP | 2003-507165 A | 2/2003 |
| JP | 2006-104211 A | 4/2006 |
| JP | 2007-526224 A | 9/2007 |
| JP | 4130678 B2 * | 8/2008 |
| JP | 2016-503037 A | 2/2016 |
| JP | 2018-177724 A | 11/2018 |
| JP | 2018-177725 A | 11/2018 |
| WO | WO 01/12139 A1 | 2/2001 |
| WO | WO 01/12335 A1 | 2/2001 |

OTHER PUBLICATIONS

International Search Report dated Jun. 19, 2018 in PCT/JP2018/015981 filed on Apr. 18, 2018.
"Hiding Flaws with Air-Touch Foundation SK2", 2007 [retrieved Jun. 5, 2018], URL: https://plaza.rakuten.co.jp/lazymom/diary/200711160001/?scid=wi_big_amp_diary_next, 3 total pages.
"SK-II Air Touch Foundation", Mintel GNDP ID No. 600036, 2006 [retrieved Jun. 4, 2018], URL: http://www.gnpd.com/global-new-products-database, 3 total pages.

(Continued)

*Primary Examiner* — Danah Al-Awadi
(74) *Attorney, Agent, or Firm* — Oblon, McClelland, Maier & Neustadt, L.L.P.

(57) ABSTRACT

Provided is a coating having a uniform and strong UV protective effect over the entire skin.

A method for producing a UV protective coating on skin comprising a step of applying a composition comprising a UV protective agent to the skin, and a step of electrostatically spraying a composition comprising component (a) and component (b) directly onto the skin to form a coating on the skin, in this order or vice versa:

(a) one or more volatile substances selected from the group consisting of water, an alcohol and a ketone, (b) a polymer having a film-forming ability.

14 Claims, 1 Drawing Sheet

(56) References Cited

OTHER PUBLICATIONS

Extended European Search Report dated Nov. 13, 2020 in European Patent Application No. 18787997.8, 8 pages.
Anonymous, "Makeup Setting Spray," Database GNPD[Online] MINTEL, Database accesion No. 3377203, Retrieved from the Internet [URL: www.gnpd.com], Aug. 18, 2015, XP055578800, 3 pages.
Database GNPD[Online] MINTEL; Jan. 27, 2015, anonymous: "Powder Foudation SPF25 PA++", XP055871887, Database accesion No. 2941163.
Qiu Bingyi, et al, "Modern Cosmetic Science and Technology," China Light Industry Press Ltd., Mar. 31, 2016, 4 pages (with machine-generated English concise explanation).
"SOFINA Primaviasta Powder Foundation UV BO01," Kao Corporation, Cosmetic J20110883, [URL: https:www.nmpa.gov.cn/datasearch/search-info.html?nmpa=aWQ9NjQzNDQmaXR1bU1kPTJjOWJhMzg0NzU5YzklNzcwMTc10WNkYzdlZmMwNDQz], Chinese National Drug Administration, Dec. 6, 2011, 6 pages (with machine-generated English concise explanation).
Yang Mingbo, et al., "Plastic molding technology". China Light Industry Press Ltd., Jun. 30. 2014, pp. 165-169 (with English abstract and unedited computer generated partial English translation).

* cited by examiner

METHOD FOR PRODUCING UV PROTECTIVE COATING

FIELD OF THE INVENTION

The present invention relates to a method of forming a UV protective coating on the skin.

BACKGROUND OF THE INVENTION

Conventionally, sunscreen cosmetics have been formulated with ultraviolet (UV) protective agents in order to block UV radiation to the skin and obtain high SPF (Sun protection Factor) values.

However, cosmetics containing these UV protective agents have drawbacks in that they have low water resistance and perspiration resistance and disappear from the skin due to perspiration or the like. In addition, since there are many irregularities on the skin, the coating is not uniform, and the SPF value is low at a place where the coating is thin. Further, there is an issue that the coating disappears due to contact with clothes or skin such as fingers. To cope with such issues, techniques for blending organosilicone polymers, water-swellable clay minerals, PVP/alkyl copolymers, and the like in cosmetics are known (Patent Literature 1 to 3).

Various methods are known for forming coatings by electrostatic spraying. For example, Patent Literature 4 discloses a method for treating skin comprising electrostatically spraying the skin with compositions. The composition used in the method contains a liquid-insulating material, a conductive material, a particulate powder material, and a thickener. Typically, a cosmetic product or a skincare composition containing a pigment is used as the composition. Specifically, a cosmetic foundation is used as the composition. That is, the inventions described in Patent Literature 4 primarily envision cosmetic purposes by electrostatically spraying a cosmetic foundation to cosmetically decorate the skin.

Patent Literature 5 discloses disposable cartridges for use in electrostatic spraying devices for cosmetics. The electrostatic spraying device is of a hand-held and self-contained type. This electrostatic spraying device is used for spraying cosmetic foundations in the same manner as the Patent Literature 4 above.

(Patent Literature 1) JP-A-hei 5-262634
(Patent Literature 2) JP-A-hei 7-258055
(Patent Literature 3) JP-A-hei 8-259430
(Patent Literature 4) JP-A-2006-104211
(Patent Literature 5) JP-A-2003-507165

SUMMARY OF THE INVENTION

The present invention provides a method for producing a UV protective coating on skin comprising a step of applying a composition comprising a UV protective agent to the skin, and a step of electrostatically spraying a composition comprising component (a) and component (b) directly onto the skin to form a coating on the skin, in this order or vice versa:

(a) one or more volatile substances selected from the group consisting of water, an alcohol and a ketone, (b) a polymer having a film-forming ability.

DETAILED DESCRIPTION OF THE INVENTION

However, even with the techniques of Patent Literatures 1 to 3, a uniform coating is not formed due to a large number of irregularities on the skin, and the SPF-value on the skin is not uniform because the UV protective agent in the coating is not uniformly distributed. In order to obtain a sufficient SPF value, it is necessary to thicken the coating, but if so, there is an issue of impairing transparency.

In addition, the coatings formed by electrostatic spraying as described in Patent Literatures 4 and 5 were not sufficiently adherent to the skin, and they caused color shifting of the foundation by contacting clothes or skin.

Accordingly, the present invention provides a novel means to form UV protective coatings that are not only superior in UV protection, but also uniform and excellent in durability without forming thicker coatings.

The present inventor has conducted extensive studies to form a coating having an excellent UV protection on the skin, and has found that the coating formed on the skin is not easily lost by contact with clothes, skin, water or the like, has a good feel and appearance, and has drastically improved the UV protective effect by using a step of applying the composition containing a UV protective agent to the skin and a step of electrostatically spraying the composition containing (a) a volatile substance and (b) a polymer having a film-forming ability directly onto the skin, thereby completing the present invention.

According to the present invention, the SPF value is drastically improved as compared with applying the UV protective agent alone to the skin, and a coating with excellent UV protective effect is formed on the skin. The formed coating has not only excellent water resistance and sweat resistance, but also excellent durability that is not easily lost in contact with skin or clothing, and exerts a good feel and appearance. In addition, when a UV protective agent is applied to the skin alone, the application is not uniform due to irregularities of the skin, and the UV protective effect is not uniformly obtained on the skin, but according to the present invention, a uniform coating is formed on the skin, and therefore, a uniform UV protective effect is obtained.

The present invention comprises the steps of applying to the skin a UV protective composition (hereinafter referred to as a UV composition) and electrostatically spraying the composition containing component (a) and component (b) directly onto the skin to form a coating on the skin. First, a step of applying the UV composition will be described.

(a) one or more volatile substances selected from the group consisting of water, an alcohol and a ketone, (b) a polymer having a film-forming ability.

As the UV protective agent used in the UV composition, a UV absorber, particularly an organic UV absorber, is preferable. The organic UV absorber is preferably oil-soluble, and includes a benzoic acid-based UV absorber, an anthranilic acid-based UV absorber, a salicylic acid-based UV absorber, a cinnamic acid-based UV absorber, a benzophenone-based UV absorber, and a triazine-based UV absorber.

Examples of the benzoic acid-based UV absorber include para-aminobenzoic acid (hereinafter, abbreviated as PABA), glyceryl PABA, ethyldihydroxypropyl PABA, N-ethoxylate PABA ethyl ester, N-dimethyl PABA ethyl ester, N-dimethyl PABA butyl ester, N-dimethyl PABA amyl ester, octyl dimethyl PABA, and hexyl diethylamino hydroxybenzoyl benzoate. From the viewpoint of suppressing stickiness while enhancing the UV absorption effect, para-aminobenzoic acid and hexyl diethylaminohydroxybenzoyl benzoate are preferable, and hexyl diethylaminohydroxybenzoyl benzoate is more preferable.

Examples of the anthranilic acid-based UV absorber include homomenthyl-N-acetylanthranilate.

Examples of the salicylic acid-based UV absorber include amyl salicylate, menthyl salicylate, homomenthyl salicylate, octyl salicylate, phenyl salicylate, benzyl salicylate, and p-isopropanol phenyl salicylate.

Examples of the cinnamic acid-based UV absorber include ethyl-4-isopropylcinnamate, ethyl-2,4-diisopropyl-cinnamate, methyl-2,4-diisopropylcinnamate, propyl-p-methoxycinnamate, isopropyl-p-methoxycinnamate, iso-amyl-p-methoxycinnamate, 2-ethylhexyl-p-methoxycinnamate, 2-ethoxyethyl-p-methoxycinnamate, cyclohexyl-p-methoxycinnamate, ethyl-α-cyano-β-phenyl-cinnamate, 2-ethylhexyl-α-cyano-β-phenylcinnamate, glyceryl mono-2-ethylhexanoyl di-p-methoxycinnamate. Among these, one or more selected from 2-ethylhexyl-p-methoxycinnamate is preferable, and 2-ethylhexyl-p-methoxycinnamate is more preferable from the viewpoint of enhancing the UV absorption effect.

Examples of the benzophenone-based UV absorber include 2,4-dihydroxybenzophenone, 2,2'-dihydroxy-4-methoxybenzophenone, 2,2'-dihydroxy-4,4'-dihydroxybenzophenone, 2-hydroxy-4-methoxybenzophenone, 2-hydroxy-4-methoxy-4'-methylbenzophenone, 2-hydroxy-4-methoxybenzophenone, 4-phenylbenzophenone, 2-ethylhexyl-4'-phenylbenzophenone-2-carboxylate, 2-hydroxy-4-n-octoxybenzophenone, and 4-hydroxy-3-carboxybenzophenone.

As the triazine-based UV absorber, from the viewpoint of enhancing the UV absorption effect, one or more selected from the group consisting of 2,4,6-tris[4-(2-ethylhexyloxy-carbonyl)anilino]-1,3,5-triazine, 2,4-bis-[{4-(2-ethylhexyloxy)-2-hydroxy}-phenyl]-6-(4-methoxypheny 1)-1,3,5-triazine and the like are preferable.

Examples of the other UV absorbers include 3-(4'-methylbenzylidene)-dl-camphor, 3-benzylidene-dl-camphor, ethyl urocanate, 2-phenyl-5-methylbenzoxazole, 2-(2'-hydroxy-5-t-octylphenyl)benzotriazole, dibenzarazine, dianisoylmethane, 4-methoxy-4'-t-butyldibenzoyl methane, 5-(3,3-dimethyl-2-norbonylidene)-3-pentane-2-one, benzene-bis-1,3-diketone derivatives as described inJP-A-hei 2-212579, and benzoylpinacolone derivatives as described in JP-A-hei 3-220153.

The UV protective agent preferably contains a UV absorber from the viewpoint of enhancing the UV protective effect, and among these, preferably contains at least one kind selected from a benzoic acid-based UV absorber, a benzophenone-based UV absorber, a cinnamic acid-based UV absorber, a triazine-based UV absorber, more preferably contains at least one kind selected from a benzoic acid-based UV absorber, a cinnamic acid-based UV absorber, and a triazine-based UV absorber, and more preferably contains at least two kinds selected from the group consisting of a benzoic acid-based UV absorber, a cinnamic acid-based UV absorber, and a triazine-based UV absorber.

The UV protective agent can be used in combination of one kind or two or more kinds, and the combination and the content thereof are determined according to the UV protective effect. From the viewpoint of further exhibiting the UV protective effect, the content of the UV protective agent is preferably 0.1 mass % or more, more preferably 1 mass % or more, even more preferably 5 mass % or more, and even more preferably 10 mass % or more in the UV composition. In addition, from the viewpoint of suppressing stickiness and imparting a dry feeling, the content of the UV protective agent is preferably 30 mass % or less, more preferably 25 mass % or less, even more preferably 20 mass % or less, and even more preferably 18 mass % or less in the UV composition.

The UV composition may contain an oil in a liquid state at 20° C. other than the UV protective agent for the purpose of dissolving the UV protective agent and for the purpose of improving the adhesivity to the skin and durability of the formed coating.

Examples of the oil in a liquid state at 20° C. include a linear or branched hydrocarbon oil such as liquid paraffin, light isoparaffin, liquid isoparaffin, squalane, and squalene, a vegetable oil such as a jojoba oil, and an olive oil, an animal oil such as liquid lanolin, an ester oil such as a monoalcohol fatty acid ester, and a polyvalent alcohol fatty acid ester, a silicone oil such as dimethylpolysiloxane, dimethylcyclopolysiloxane, methylphenylpolysiloxane, methylhydropolysiloxane, and a higher alcohol modified organopolysiloxane. Among these, from the viewpoint of impression from use such as smoothness at the time of application, a polar oil such as a hydrocarbon oil, an ester oil, a vegetable oil containing a triglyceride, or the like, or a silicone oil is preferable, and one or more selected from the group consisting of a hydrocarbon oil, an ester oil, and a silicone oil are more preferable. In addition, one or more liquid oils selected from these can be used in combination.

Examples of the hydrocarbon oil include liquid paraffin, squalane, squalene, n-octane, n-heptane, cyclohexane, light isoparaffin, and liquid isoparaffin, and liquid paraffin and squalane are preferable from the viewpoint of impression from use. In addition, from the viewpoint of adhering the electrostatically sprayed coating to the skin, the viscosity of the hydrocarbon oil at 30° C. is preferably 10 mPa·s or more, more preferably 30 mPa·s or more. From this viewpoint, the total content of isododecane, isohexadecane, hydrogenated polyisobutene having viscosity of less than 10 mPa·s at 30° C. in the UV composition is preferably 10 mass % or less, more preferably 5 mass % or less, even more preferably 1 mass % or less, even more preferably 0.5 mass % or less, and these may not be contained.

Similarly, from the viewpoint of adhering the formed coating to the skin, the viscosity of the ester oil and the silicone oil at 30° C. is preferably 10 mPa·s or more, more preferably 30 mPa·s or more.

The viscosity here is measured at 30° C. with a BM-type viscometer (manufactured by Tokimek Corporation, measurement conditions: Rotor No. 1, 60 rpm, 1 minute).

From the same viewpoint, the total content of ether oils such as cetyl-1,3-dimethylbutyl ether, dicapryl ether, dilauryl ether, diisostearyl ether, in the UV composition is preferably 10 mass % or less, more preferably 5 mass % or less, and even more preferably 1 mass % or less.

Examples of the ester oil include an ester consisting of a linear or branched chain fatty acid and a linear or branched chain alcohol or a polyvalent alcohol. Specifically, isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethyleneglycol di(2-ethylhexanoate), dipentaerythritol fatty acid ester, N-alkylglycol monoisostearate, neopentylglycol dicaprate, diisostearyl malate, glyceryl di(2-heptylundecanoate), trimethylolpropane tri(2-ethylhexanoate), trimethylolpropane triisostearate, pentaerythritol tetra(2-ethylhexanoate), glyceryl tri(2-ethylhexanoate), trimethylolpropane triisostearate, cetyl 2-ethylhexanoate, 2-ethylhexyl palmitate, diethylhexyl naphthalenedicarboxylate, (C12-15)alkyl benzoate, cetearyl isononanoate, caprylic/capric triglyceride, dicaprylic/capric butyleneglycol, glyceryl trilaurate, glyceryltrimyristate, glyceryltripalmitate, glyceryltriisostearate, glyceryl tri(2-heptylundecanoate), glyceryl tribehenate, glyceryl tricocoate, castor oil fatty acid methyl ester, oleyl oleate, 2-heptylundecyl palmitate, diisobutyl adipate, N-lauryol-L-glutamate-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, di(2-ethylhexyl) succinate, triethyl citrate, 2-ethylhexyl para-methoxycinnamate, and tripropylene glycol dipivalate.

Among these, from the viewpoint of adhering the formed coating to the skin and in terms of excellent feeling of the coating upon application to the skin, at least one selected from the group consisting of octyldodecyl myristate, myristyl myristate, isocetyl stearate, isocetyl isostearate, cetearyl isononanoate, diisobutyl adipate, di-2-ethylhexyl sebacate, isopropyl myristate, isopropyl palmitate, diisostearyl malate, neopentylglycol dicaprate, (C12-15)alkyl benzoate, and caprylic/capric triglyceride, is preferable. At least one selected from the group consisting of isopropyl myristate, isopropyl palmitate, diisostearyl malate, neopentylglycol dicaprate, (C12-15)alkyl benzoate, and caprylic/capric triglyceride is more preferable. It is further preferable to contain one or more selected from the group consisting of neopentylglycol dicaprate, (C12-15)alkyl benzoate, and caprylic/capric triglyceride.

As the triglyceride, a fatty acid triglyceride is preferable, and the triglyceride is included in, for example, an olive oil, a jojoba oil, a macademia nut oil, a medform oil, a castor oil, a safflower oil, a sunflower oil, an avocado oil, a canola oil, a ginseng oil, a rice germ oil, and a rice bran oil.

Examples of the silicone oil include dimethylpolysiloxane, methylcyclopolysiloxane, methylphenylpolysiloxane, methylhydrogenpolysiloxane, higher alcohol modified organopolysiloxane.

The kinematic viscosity of the silicone oil at 25° C. is preferably 3 mm$^2$ per second, more preferably 4 mm$^2$ per second, more preferably 5 mm$^2$ per second or more, more preferably 30 mm$^2$ per second or less, more preferably 20 mm$^2$ per second or less, and even more preferably 10 mm$^2$ per second or less, from the viewpoint of adhering the formed coating to the skin.

Among these, it is preferable to contain methylpolysiloxane from the viewpoint of adhering the formed coating to the skin.

The content of the liquid oil in the UV composition is preferably 0.1 mass % or more, more preferably 0.5 mass % or more, and even more preferably 5 mass % or more. It is preferably 90 mass % or less. The content of the liquid oil in the UV composition is preferably 0.1 mass % or more and 90 mass % or less, more preferably 0.5 mass % or more and 70 mass % or less. More preferably, it is 50 mass % or less.

The UV composition may further contain water and a polyol. When water or polyol is contained, the form of the UV composition includes emulsions such as O/W emulsions and W/O emulsions.

When a polyol is contained, examples of the polyol include an alkylene glycol such as ethylene glycol, propylene glycol, 1,3-propanediol, and 1,3-butanediol; a polyalkylene glycol such as diethylene glycol, dipropylene glycol, polyethylene glycol, and polypropylene glycol; a glycerin such as glycerin, diglycerin, and triglycerin. Among these, one or more selected from the group consisting of ethylene glycol, propylene glycol, 1,3-butanediol, dipropylene glycol, polyethylene glycol, glycerin, and diglycerin are preferable, one or more selected from the group consisting of propylene glycol, 1,3-butanediol, and glycerin are more preferable, and one or two selected from the group consisting of propylene glycol and 1,3-butanediol are even more preferable from the viewpoint of impression from use such as smoothness.

The UV composition contains a UV protective agent and the aforementioned components and may be in the form of an oily composition, a water-in-oil emulsifying composition, an oil-in-water emulsifying composition, and the like. The shape may be a liquid, an emulsion, a cream, a paste, a solid, a multilayer, or the like. Components other than the UV protective agent which can be incorporated in the UV composition include, in addition to the liquid oil, a solid oil, an emulsifier, water, a polyol, a colored pigment, a constitution pigment, a dye, a perfume, an antioxidant, a preservative, and various vitamins.

In the present invention, a composition which is electrostatically sprayed directly onto the skin (hereinafter sometimes referred to as a spraying composition) is a composition which comprises the following components (a) and (b):

(a) one or more volatile substances selected from the group consisting of water, an alcohol and a ketone;

(b) a polymer having a film-forming ability.

The (a) volatile substance is a substance having volatility in a liquid state. In the spraying composition, component (a) is discharged from the nozzle tip toward the skin after sufficiently charging the spraying composition placed in the electric field, and when component (a) evaporates, the charge density of the spraying composition becomes excessive, and component (a) evaporates further while being further refined by Coulomb repulsion, and is blended for the purpose of forming a finally dried coating. For this purpose, the volatile substance preferably has a vapor pressure at 20° C. of 0.01 kPa or more and 106.66 kPa or less, more preferably 0.13 kPa or more and 66.66 kPa or less, even more preferably 0.67 kPa or more and 40.00 kPa or less, and even more preferably 1.33 kPa or more and 40.00 kPa or less.

Among the (a) volatile substance, a monovalent chain aliphatic alcohol, a monovalent cyclic aliphatic alcohol, and a monovalent aromatic alcohol are suitable for use as alcohol. The monovalent chain aliphatic alcohol includes C1-C6 alcohol, the monovalent cyclic alcohol includes C4-C6 cyclic alcohol, and the monovalent aromatic alcohol includes benzyl alcohol, phenylethyl alcohol. Specific examples thereof include ethanol, isopropyl alcohol, butyl alcohol, phenylethyl alcohol, n-propanol, n-pentanol. One or more selected from these alcohols can be used.

Among the (a) volatile substance, examples of the ketone include a C1-C4 dialkyl ketone, for example, acetone, methyl ethyl ketone, methyl isobutyl ketone. These ketones can be used alone or in combination of two or more.

The (a) volatile substance is more preferably one or more selected from the group consisting of ethanol, isopropyl alcohol, butyl alcohol and water, more preferably one or more selected from the group consisting of ethanol and butyl alcohol, and even more preferably a volatile substance containing ethanol.

The content of component (a) in the spray composition is preferably 50 mass % or more, more preferably 55 mass % or more, and even more preferably 60 mass or more. In addition, the content of component (a) is preferably 98 mass % or less, more preferably 96 mass % or less, and even more preferably 94 mass % or less. The content of component (a) in the spraying composition is preferably 50 mass % or more and 98 mass % or less, more preferably 55 mass % or more and 96 mass % or less, and even more preferably 60 mass % or more and 94 mass % or less. By containing component (a) in the spraying composition in this amount, the spraying composition can be sufficiently volatilized when the electrostatic spraying is performed.

The content of ethanol is preferably 50 mass % or more, more preferably 65 mass % or more, and even more preferably 80 mass % or more, based on the total amount of the (a) volatile substance. It is preferable that the content is 100 mass % or less. The content of ethanol is preferably 50 mass % or more and 100 mass % or less, more preferably 65 mass % or more and 100 mass % or less, and even more preferably 80 mass % or more and 100 mass % or less, based on the total amount of the (a) volatile substance.

The (b) polymer having a film-forming ability generally refers to a substance which can be dissolved in the (a) volatile substance. Here, "be dissolved" means a dispersed state at 20° C., and the dispersed state is a visually uniform state, preferably in a visually transparent or translucent state.

As the polymer having a film forming ability, a polymer suitable for the nature of the (a) volatile substance is used. Specifically, a polymer having a film-forming ability is roughly classified into a water-soluble polymer and a water-insoluble polymer. As used herein, the term "water-soluble polymer" means a polymer having a property in which, after weighing the polymer 1 g at 1 atm and 23° C., the polymer is immersed in 10 g of ion-exchanged water, and 0.5 g or more of the immersed polymer is dissolved in water after a lapse of 24 hours. Meanwhile, the "water-insoluble polymer" in the present specification means a polymer having a property that 0.5 g or more of the polymer immersed in 10 g of ion-exchanged water is not dissolved after 24 hours after weighing the polymer 1 g at 1 atm and 23° C.

Examples of a polymer that is water-soluble and has a film-forming ability include a natural polymer such as pullulan, hyaluronic acid, chondroitin sulfate, poly-γ-glutamic acid, modified corn starch, β-glucan, a gluco-oligosaccharide, a mucopolysaccharide (e.g., heparin, and keratosulfuric acid), pectin, xylan, lignin, glucomannan, galacturonic acid, psyllium seed gum, tamarind seed gum, arabic gum, tragacanth gum, soy water-soluble polysaccharide, alginic acid, carrageenan, laminaran, agar (agarose), fucoidan, methylcellulose, hydroxypropyl cellulose, and hydroxypropyl methylcellulose; and a synthetic polymer such as a partially saponified polyvinyl alcohol (not using in combination with a crosslinking agent), a low saponified polyvinyl alcohol, polyvinylpyrrolidone (PVP), polyethylene oxide, and sodium polyacrylate. These water-soluble polymers can be used alone or in combination of two or more. Among these water-soluble polymers, pullulan, and a synthetic polymer such as a partially saponified polyvinyl alcohol, a low saponified polyvinyl alcohol, polyvinyl pyrrolidone, and polyethylene oxide are preferably used from the viewpoint of easy production of the coating. When polyethylene oxide is used as the water-soluble polymer, its number average molecular weight is preferably from 50,000 to 3,000,000, more preferably from 100,000 to 2,500,000.

Meanwhile, examples of a polymer having a film-forming ability which is insoluble in water include a fully saponified polyvinyl alcohol which can be insolubilized after a coating is formed, a partially saponified polyvinyl alcohol which can be crosslinked by using in combination with a crosslinking agent after a coating is formed, an oxazoline-modified silicone such as poly(N-propanoylethyleneimine)graft-dimethylsiloxane/γ-aminopropyl methylsiloxane copolymer, polyvinyl acetal diethylaminoacetate, Zein (a main component of corn protein), polyester, polylactic acid (PLA), acrylic resin (e.g., a polyacrylonitrile resin, and a polymethacrylic acid resin), a polystyrene resin, a polyvinyl butyral resin, a polyethylene terephthalate resin, a polybutylene terephthalate resin, a polyurethane resin, a polyamide resin, a polyimide resin, a polyamide-imide resin. These water-insoluble polymers can be used alone or in combination of two or more. Among these water-insoluble polymers, it is preferable to use a fully saponified polyvinyl alcohol that can be insolubilized after forming the coating, a partially saponified polyvinyl alcohol that can be crosslinked by using in combination with a cross-linking agent after forming the coating, polyvinyl butyral resin, polyurethane resin, oxazoline-modified silicone such as poly (N-propanoyl ethyleneimine) graft-dimethylsiloxane/γ-aminopropylmethylsiloxane copolymer, water-soluble polyester, and Zein, and more preferably one or more selected from the group consisting of a polyvinyl butyral resin and a polyurethane resin.

The content of component (b) in the spraying composition is preferably 2 mass % or more, more preferably 4 mass % or more, and even more preferably 6 mass % or more. In addition, the content of component (b) is preferably 50 mass or less, more preferably 45 mass % or less, and even more preferably 40 mass % or less. The content of component (b) in the spraying composition is preferably 2 mass % or more and 50 mass % or less, more preferably 4 mass % or more and 45 mass % or less, and even more preferably 6 mass % or more and 40 mass % or less. By containing component (b) in this amount in the spraying composition, a desired coating can be efficiently formed.

The content ratio of component (a) and component (b) in the spraying composition, ((a)/(b)), is preferably 0.5 or more and 40 or less, more preferably 1 or more and 30 or less, and even more preferably 2 or more and 25 or less, from the viewpoint that component (a) can be sufficiently volatilized when the electrostatic spraying is performed.

In addition, the content ratio of (a) ethanol and component (b) in the spraying composition, ((a)/(b)), is preferably from 0.5 to 40, more preferably from 1 to 30, and even more preferably from 2 to 25, from the viewpoint that component (a) can be sufficiently volatilized when the electrostatic spraying is performed.

In addition, glycols may be contained in the spraying composition. Examples of the glycol include ethylene glycol, propylene glycol, butylene glycol, diethylene glycol, dipropylene glycol, and polypropylene glycol. From the viewpoint that component (a) can be sufficiently volatilized when the electrostatic spraying is performed, component (a) is preferably 10 mass % or less, more preferably 3 mass % or less, preferably 1 mass % or less, or substantially free.

The spraying composition may contain only component (a) and component (b) described above, or may contain other components in addition to component (a) and component (b). Examples of the other components include a plasticizer of the (b) polymer having a film-forming ability, a colored pigment, a constitutive pigment, a dye, a surfactant, a perfume, a repellent, an antioxidant, a stabilizer, a preservative, and various vitamins. When other components are contained in the spray composition, the content of the other components is preferably 0.1 mass % or more and 30 mass % or less, and more preferably 0.5 mass % or more and 20 mass % or less.

The present invention includes the step of electrostatically spraying the spraying composition onto the skin to form a coating on the skin, which is performed before or after the step of applying the UV composition.

When the electrostatic spraying is performed, a composition having a viscosity at 25° C. of 1 mPa·s or more, more preferably 10 mPa·s or more, more preferably 50 mPa·s or more is used as the spraying composition. In addition, a composition having a viscosity at 25° C. of 5,000 mPa·s or less, more preferably 2,000 mPa·s or less, and even more preferably 1,500 mPa·s or less is used. The viscosity of the spraying composition at 25° C. is preferably 1 mPa·s or more and 5,000 mPa·s or less, more preferably not less than 10 mPa·s and not more than 2,000 mPa·s, and more preferably 50 mPa·s or more and 1,500 mPa·s or less. By using a spraying composition having a viscosity in this range, it is possible to successfully form a porous coating, in particular a porous coating consisting of a fiber deposit, by means of an electrostatic spraying. The formation of the porous coating is advantageous from the viewpoint of enhancing the UV protective effect, adhesivity of the coating, durability of the coating, feel, appearance, and prevention of skin evaporation. The viscosity of the spraying composition is measured at 25° C. using a type-E viscometer. As the type-E viscometer, for example, an E-type viscometer manufactured by Tokyo Instrument Co., Ltd. can be used. In this case, the rotor No. 43 can be used as the rotor.

The spraying composition may be sprayed by electrostatic spraying directly onto the site of the human skin to be UV protected. Electrostatic spraying involves electrostatically spraying the spraying composition onto the skin using an electrostatic spraying device. An electrostatic spraying device basically includes a container containing the composition, a nozzle for discharging the composition, a supply device for supplying the composition contained in the container to the nozzle, and a power supply for applying a voltage to the nozzle.

Figure 1:
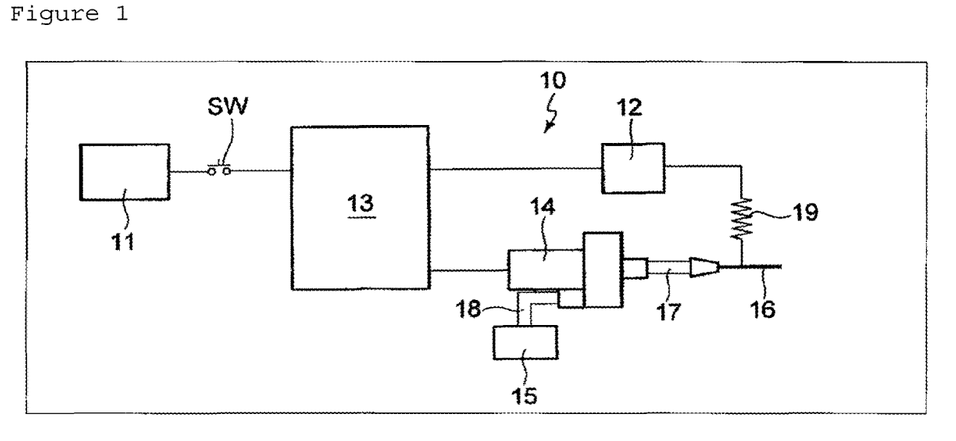
FIG. 1 is a schematic diagram showing the construction of an electrostatic spraying device suitable for use in the present invention.

FIG. 1 is a schematic diagram showing a configuration of an electrostatic spraying device preferably used in the present invention. The electrostatic spraying device 10 shown in the figure includes a low voltage power supply 11. The low-voltage power supply 11 can generate a voltage of several volts and below 20 volts. For the purpose of enhancing the portability of the electrostatic spraying device 10, the low voltage power supply 11 preferably comprises one or more batteries. Further, by using a battery as the low voltage power supply 11, there is an advantage that replacement can be easily performed as necessary. Instead of the battery, an AC adapter or the like can be used as the low-voltage power supply 11.

The electrostatic spraying device 10 also includes a high voltage power supply 12. The high voltage power supply 12 is connected to the low voltage power supply 11, and includes an electric circuit (not shown) for boosting a voltage generated by the low voltage power supply 11 to a high voltage. The booster electric circuit is generally composed of a transformer, a capacitor, a semiconductor element, and the like.

The electrostatic spraying device 10 further comprises an auxiliary electrical circuit 13. The auxiliary electric circuit 13 is interposed between the low-voltage power supply 11 and the high-voltage power supply 12, and has a function of adjusting the voltage of the low-voltage power supply 11 to stably operate the high-voltage power supply 12. Further, the auxiliary electric circuit 13 has a function of controlling the number of revolutions of a motor provided in a microgear pump 14, which will be described later. By controlling the rotation speed of the motor, the supply amount of the spraying composition from the container 15 of the spraying composition described later to the microgear pump 14 is controlled. A switch SW is mounted between the auxiliary electric circuit 13 and the low-voltage power supply 11 so that the electrostatic spraying device 10 can be turned on and off by turning the switch SW on and off.

The electrostatic spraying device 10 further comprises a nozzle 16. The nozzle 16 is made of a conductive material such as metal or a non-conductive material such as plastic, rubber, ceramic, or the like, and has a shape capable of discharging the spraying composition from the tip thereof. A minute space through which the spraying composition flows is formed in the nozzle 16 along the longitudinal direction of the nozzle 16. The size of the cross section of the micro space is preferably 100 μm or more and 1000 μm or less in terms of diameter. The nozzle 16 communicates with the microgear pump 14 via a pipe 17. The pipe 17 may be conductive or non-conductive. The nozzle 16 is electrically connected to the high-voltage power supply 12. This makes it possible to apply a high voltage to the nozzle 16. In this case, in order to prevent an excessive current from flowing when a human body directly touches the nozzle 16, the nozzle 16 and the high voltage power supply 12 are electrically connected via a current limiting resistor 19.

The microgear pump 14, which communicates with the nozzle 16 via a pipe 17, functions as a supply device for supplying the nozzle 16 with the spraying composition contained in the container 15. The microgear pump 14 is operated by receiving a power supply from the low voltage power supply 11. The microgear pump 14 is configured to supply a predetermined amount of the spraying composition to the nozzle 16 under the control of the auxiliary electric circuit 13.

A container 15 is connected to the microgear pump 14 via a flexible pipe 18. Contained in the container 15 is the spraying composition. The container 15 preferably has a cartridge-type replaceable configuration.

Figure 2:
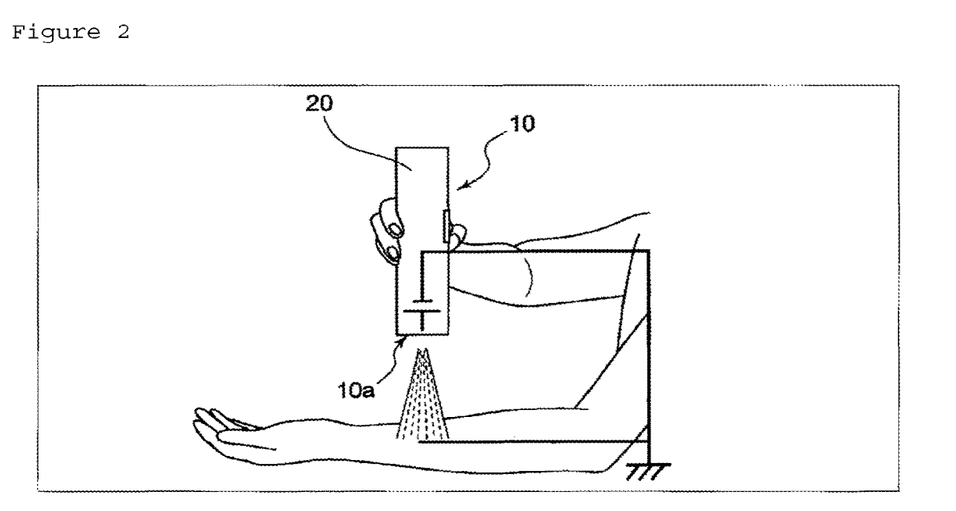
FIG. 2 is a schematic diagram showing the operation of an electrostatic spraying using an electrostatic spraying device.

The electrostatic spraying device 10 having the above configuration can be used, for example, as shown in FIG. 2. FIG. 2 shows an electrostatic spraying device 10 of the hand-held type having a size holdable by one hand. The electrostatic spraying device 10 shown in the same figure contains all of the members of the configuration diagram shown in FIG. 1 in the cylindrical housing 20. A nozzle, not shown, is disposed at one longitudinal end 10a of the housing 20. The nozzle is disposed in the housing 20 such that the blowing direction of the composition coincides with the longitudinal direction of the housing 20 and is convex toward the skin side. By arranging the nozzle tip so as to be convex toward the skin in the longitudinal direction of the housing 20, the spraying composition hardly adheres to the housing, and the coating can be stably formed.

When the user intends to operate the electrostatic spraying device 10, the user, i.e., the person who forms the coating on the site on the skin to be UV protected by the electrostatic spray, holds the device 10 by hand and directs one end 10a of the device 10, on which a nozzle, not shown, is located, to the application site where the electrostatic spray is to be performed. In FIG. 2, one end 10a of the electrostatic spraying device 10 is shown pointing inside the user's forearm. In this state, the device 10 is switched on to perform the electrostatic spraying. When the device 10 is powered on, an electric field is generated between the nozzle and the skin. In the embodiment shown in FIG. 2, a positive high voltage is applied to the nozzle and the skin becomes the negative electrode. When an electric field is generated between the nozzle and the skin, the spraying composition at the tip of the nozzle is polarized by electrostatic induction so that the tip portion becomes conical, and droplets of the spraying composition charged from the tip of the cone are discharged into the air toward the skin along the electric field. When component (a) (a solvent) evaporates from the spraying composition discharged into the space and charged, the charge density on the surface of the spraying composition becomes excessive, and spreads into the space by repeated refinement by Coulomb repulsion force, and reaches the skin. In this case, by appropriately adjusting the viscosity of the spraying composition, the sprayed composition can reach the application site in the form of droplets. Alternatively, while the spraying composition is discharged to a space, it is also possible to deposit a fiber formed by stretch deformation by an electric potential difference onto an application site, with a volatile substance (solvent) being evaporated out of the droplet and a film-forming polymer (solute) being solidified. For example, increasing the viscosity of the spraying composition facilitates deposition of the composition in the form of fibers at the site of application. This forms a porous coating of a fiber deposit on the surface of the application site. The porous coating of the fiber deposit containing a UV protective agent can also be formed by adjusting the distance between the nozzle and the skin and the voltage applied to the nozzle.

During electrostatic spraying, a high electric potential difference is created between the nozzle and the skin. However, because of very large impedance, an extremely small amount of current flows through the human body. For example, the present inventor has confirmed that the current flowing through the human body during the electrostatic spraying step is several orders of magnitude smaller than the current flowing through the human body due to static electricity generated during normal living.

When a fiber deposit is formed by an electrostatic spraying, the thickness of the fiber is preferably 10 nm or more, more preferably 50 nm or more, when expressed as a circle equivalent diameter. The thickness is preferably 3,000 nm or less, and more preferably 1,000 nm or less. The thickness of the fiber can be measured by observing the fiber at a magnification of 10,000 by, for example, scanning electron microscopy (SEM) observation, removing defects (clumps of fibers, crossing portions of fibers, and droplets) from the two-dimensional image, arbitrarily selecting 10 fibers, drawing a line orthogonal to the longitudinal direction of the fiber, and directly reading the fiber diameter.

The fibers are continuous fibers of infinite length in principle of manufacture, but preferably have a length of at least 100 times or more the thickness of the fibers. In the present specification, a fiber having a length of 100 times or more of the thickness of the fiber is defined as a "continuous fiber". The coating produced by the electrostatic spraying is preferably a porous discontinuous coating composed of a deposit of continuous fibers. Such a form of coating not only can be handled as a single sheet as an aggregate, but has the advantage that it has a very soft property, and it is difficult to be separated even when a shearing force is applied to it, and it is excellent in the followability to the body movement. In addition, there is an advantage that it is excellent in the dissipation of sweat generated from the skin. Further, there is an advantage that the coating can be easily peeled off. Meanwhile, a continuous coating without pores is not easy to peel off and has a very low sweat dissipation property, so that the skin is liable to be evaporated.

The fibrous spraying composition reaches the application site in a charged state. Since the skin is also charged as described hereinbefore, the fibers adhere to the application site by electrostatic forces. Since fine irregularities such as texture are formed on the surface of the skin, the fibers more closely adhere to the surface of the skin together with the anchoring effect due to the irregularities. When the electrostatic spraying is completed in this manner, the power of the electrostatic spraying device 10 is turned off. As a result, the electric field between the nozzle and the skin disappears, and the surface of the skin is immobilized with an electric charge. As a result, the adhesivity of the coating is further improved.

Although the above description has been directed to a porous coating consisting of a fiber deposit as a coating, the form of the coating is not limited to this, and a continuous coating without pores may be formed, or a porous coating having a form other than the fiber deposit, for example, a porous coating in which a plurality of through-holes are formed irregularly or regularly in the continuous coating, i.e., a discontinuous coating may be formed. As described hereinbefore, any shape of the coating can be formed by controlling the viscosity of the spraying composition, the distance between the nozzle and the skin, the voltage applied to the nozzle, and the like.

The distance between the nozzle and the skin also depends on the voltage applied to the nozzle, but 50 mm or more and 150 mm or less are preferable from the viewpoint of successfully forming the coating. The distance between the nozzle and the skin can be measured by a commonly used non-contact sensor or the like.

Whether the coating formed by the electrostatic spraying is porous or not, the basis weight of the coating is preferably 0.1 $g/m^2$ or more, more preferably 1 $g/m^2$ or more, and even more preferably 3 $g/m^2$ or more from the viewpoint of UV protection and durability. In addition, from the viewpoint of coating feel and appearance, it is preferable that the basis weight is 25 $g/m^2$ or less, more preferably 15 $g/m^2$ or less, and further preferably 10 $g/m^2$ or less. For example, the basis weight of the coating is preferably 0.1 $g/m^2$ or more and 25 $g/m^2$ or less, more preferably 1 $g/m^2$ or more and 15 $g/m^2$ or less, and more preferably 3 $g/m^2$ or more and 10 $g/m^2$ or less. By setting the basis weight of the coating in this manner, it is possible to effectively prevent loss of the UV protective agent at the application site while preventing peeling of the coating due to excessive thickening of the coating.

The step of electrostatic spraying to form a coating by electrostatically spraying the composition directly onto the skin means a step of electrostatically spraying onto the skin to form a coating. The step of electrostatically spraying the composition to a location other than the skin to produce a sheet of fibers and applying the sheet to the skin differs from the electrostatically spraying step described hereinbefore.

In the present invention, the step of applying a UV composition by means other than electrostatic spraying and the step of electrostatic spraying are performed in this order or vice versa. By doing so in this order, the coating formed by the electrostatic spraying step becomes more familiar to the application site, and the coating can be made highly adherent to the skin, and can be made transparent. For example, a space is less likely to be made between the edge of the coating and the skin, thereby improving the adhesivity between the coating and the skin. As a result, peeling, tear, or the like of the coating is less likely to occur. In a more preferable embodiment, when the coating is a porous coating composed of a fiber deposit, the adhesivity with the skin is high despite the high porosity, and a large capillary force is apt to be generated, and the UV protective agent in the UV composition is uniformly present on the skin surface by the capillary phenomenon, thereby enhancing the UV protective effect. Furthermore, when the fibers are fine, it is easy to make the porous coating have a high specific surface area, and it is possible to make the UV composition exist in a large amount in the deposit of the fibers.

In particular, by performing a UV composition application step by a method other than electrostatic spraying after forming a porous coating composed of a fiber deposit in the electrostatic spraying step, a UV protective agent bearing coating in which the UV composition is present between the fibers forming the porous coating and/or on the fiber surface is formed, and the UV composition also penetrates uniformly between the fibers and/or on the fiber surface, thereby dramatically improving the UV protective effect. This improves the adhesivity of the coating and maintains or improves the transparency of the coating for visual inspection. In particular, when the coating is colorless and transparent or colored and transparent, the coating becomes more difficult to visually recognize, so that the coating can appear like natural skin. In addition, when the coating is colored and transparent, the coating has a transparent feeling, so that it can appear as a part of the skin.

In particular, when the UV composition contains a polar oil, it is preferable that the UV composition contains water and a polar oil from the viewpoint of improving adhesivity of the coating to the skin, and it is preferable that the UV composition contains water and a polar oil in a total content of 40 mass % or more and 100 mass % or less. From the viewpoint of stability, the UV composition may contain a surfactant, a polymer, a thickener, or an oil agent which is in a solid state at 30° C., such as petrolatum, cetanol, stearyl alcohol, or ceramide, from the viewpoint of improving adhesivity to the skin and moisturizing performance to the coating.

Similarly, when the UV composition contains a polyol, it is preferable that the UV composition contain water and a polyol from the viewpoint of enhancing the adhesivity of the coating to the skin, and it is preferable that the UV composition contain water and a polyol in a total of 40 mass % or more and 100 mass % or less. From the viewpoint of stability, the UV composition may contain a surfactant, a polymer, a thickener, or an oil agent which is solid at 30° C., such as petrolatum, cetanol, stearyl alcohol, ceramide, or the like, from the viewpoint of improving adhesivity to the skin and moisturizing performance to the coating.

The UV composition preferably has a viscosity at 25° C. of about 100,000 mPa·s or less, preferably 30,000 mPa·s or less, more preferably 10,000 mPa·s or less from the viewpoint of improvement of adhesivity between the coating formed by the electrostatic spraying and the application site. The viscosity of the UV composition is measured by a type B viscometer (manufactured by Tokyo Industries, Ltd., TVB-10 type, measuring condition: Rotor No. 1, Rotor No. 60 rpm, 1 minute).

Various conventional cosmetic methods other than electrostatic spraying can be used to apply the UV composition to the skin. For example, by applying the composition to the skin by a method such as dropping or sprinkling, and by providing a step of spreading the composition, it becomes possible to conform to the skin or the coating, and a thin layer of the composition can be formed. The step of spreading the UV composition may employ, for example, a method such as rubbing using a finger of the user or a tool such as an applicator. The UV composition may be simply dropped or sprinkled, but by providing the spreading step, it becomes possible to conform to the skin or the coating, and the adhesivity of the coating can be sufficiently improved. Alternatively, the UV composition can be sprayed onto the skin by conventional means to form a thin layer of the composition. In this case, separate spreading is not particularly necessary, but the spreading operation after spraying is not hindered. When the UV composition is applied after the formation of the coating, sufficient UV composition is applied to the skin, and the excess composition can be removed by contacting the sheet material with the extent to which the composition is applied.

The amount of the UV composition to be applied to the skin may be an amount necessary and sufficient to improve the UV protective effect and the adhesivity between the skin and the coating. From the viewpoint of improving the UV protective effect and durability, the amount of the UV composition to be applied to the skin is such that the basis weight of the composition after the application is finished is preferably 1 $g/m^2$ or more, more preferably 3 $g/m^2$ or more, more preferably 5 $g/m^2$ or more, and even more preferably 10 $g/m^2$ or more, and is preferably 85 $g/m^2$ or less, more preferably 60 $g/m^2$ or less, even more preferably 40 $g/m^2$ or less, and even more preferably 35 $g/m^2$ or less from the viewpoint of the film feeling. For example, the amount of the UV composition to be applied to the skin is an amount such that the basis weight of the UV composition after the application is finished is preferably 5 $g/m^2$ or more and 40 $g/m^2$ or less, more preferably 10 $g/m^2$ or more and 35 $g/m^2$ or less.

In addition, the amount of the composition for applying the UV composition to the skin or the coating is preferably 5 $g/m^2$ or more, more preferably 10 $g/m^2$ or more, more preferably 15 $g/m^2$ or more, more preferably 50 $g/m^2$ or less, and more preferably 45 $g/m^2$ or less from the viewpoint of obtaining a satisfactory UV protective effect, improving the adhesivity between the skin and the coating, and improving the appearance of the UV composition.

In addition, the amount of the spray composition used is preferably an amount such that the amount of the spray composition is 1 $g/m^{-2}$ or more, more preferably 3 $g/m^{-2}$ or more, more preferably 5 $g/m^{-2}$ or more, more preferably 25 $g/m^{-2}$ or less, more preferably 15 $g/m^{-2}$ or less, and even more preferably 10 $g/m^{-2}$ or less from the viewpoint of improving the UV protective effect and durability.

The method for producing the UV protective coating according to the present invention as described hereinbefore is useful as a cosmetic method for UV protection which is not intended for surgical, therapeutic or diagnostic methods of the human body.

Although the present invention has been described above with reference to its preferred embodiment, the present invention is not limited to the embodiments described above. For example, in the embodiment described above, a person who wants to form a coating on his or her own skin holds the electrostatic spraying device 10 and generates an electric field between the conductive nozzle of the device 10 and his or her skin, but as long as an electric field is generated between the two, it is not necessary for him or her to hold the electrostatic spraying device 10.

With respect to the embodiments described above, the present invention further disclose the following methods of production of coatings.

<1> A method for producing a UV protective coating on skin comprising
  a step of applying a composition comprising a UV protective agent to the skin, and
  a step of electrostatically spraying a composition comprising component (a) and component (b) directly onto the skin to form a coating on the skin, in this order or vice versa:
    (a) one or more volatile substances selected from the group consisting of water, an alcohol and a ketone,
    (b) a polymer having a film-forming ability.
(2) The method according to <1>, comprising a step of applying the composition comprising a UV protective agent to the skin by a method other than electrostatic spraying.
<3> The method according to <1> or <2>, wherein the UV protective agent is a UV absorber, preferably an organic UV absorber.
<4> The method according to any one of <1> to <3>, wherein the electrostatic spraying is performed by using an electrostatic spraying device having a container containing the composition, a nozzle for discharging the composition therefrom, a supply device for supplying the composition contained in the container to the nozzle, and a power supply for applying a voltage to the nozzle.
<5> The method according to anyone of <1> to <4>, wherein the composition further contains an oil in a liquid state at 20° C.
<6> The method according to any one of <1> to <5>, wherein the (a) volatile substance has a vapor pressure at 20° C. of 0.01 kPa or more and 106.66 kPa or less, more preferably 0.13 kPa or more and 66.66 kPa or less, even more preferably 0.67 kPa or more and 40.00 kPa or less, and even more preferably 1.33 kPa or more and 40.00 kPa or less.
<7> The method according to any one of <1> to <6>, wherein the (a) volatile substance is an alcohol, and one or more selected from the group consisting of a monovalent chain aliphatic alcohol, a monovalent cyclic aliphatic alcohol, and a monovalent aromatic alcohol are preferable as the alcohol, and one or more selected from the group consisting of ethanol, isopropyl alcohol, butyl alcohol, phenylethyl alcohol, propanol, and pentanol are more preferable as the alcohol.
<8> The method according to any one of <1> to <7>, wherein the (a) volatile substance is one or more selected from the group consisting of ethanol, isopropyl alcohol, butyl alcohol, and water, more preferably one or two selected from the group consisting of ethanol and butyl alcohol, even more preferably a volatile substance containing ethanol, and even more preferably a volatile substance having an ethanol content of 50 mass % or more and 100 mass % or less in the volatile substance.
<9> The method according to any one of <1> to <8>, wherein the (b) polymer having a film-forming ability is a substance that can be dissolved in the (a) volatile substance, and includes a water-soluble polymer and a water-insoluble polymer, (herein the term "dissolved" means a dispersed state at 20° C., and the dispersed state is visually uniform, preferably visually transparent or translucent).
<10> The method according to <9>, wherein the water-soluble polymer having a film-forming ability is one or more water-soluble polymer selected from the group consisting of mucopolysaccharide (e.g., pullulan, hyaluronic acid, chondroitin sulfate, poly-γ-glutamic acid, a modified corn starch, β-glucan, gluco-oligosaccharide, heparin, keratosulfuric acid), a natural polymer (e.g., cellulose, pectin, xylan, lignin, glucomannan, galacturonic acid, psyllium seed gum, tamarind seed gum, arabic gum, tragacanth gum, soy water-soluble polysaccharide, alginic acid, carrageenan, laminaran, agar (agarose), fucoidan, methyl cellulose, hydroxypropyl cellulose, hydroxypropyl methylcellulose), a partially saponified polyvinyl alcohol (not using in combination with a crosslinking agent), a low saponified polyvinyl alcohol, polyvinylpyrrolidone (PVP), polyethylene oxide and sodium polyacrylate; preferably one or more water-soluble polymers selected from the group consisting of pullulan, a partially saponified polyvinyl alcohol, a low saponified polyvinyl alcohol, polyvinyl pyrrolidone, and polyethylene oxide.
<11> The method according to <9>, wherein the polymer having a film-forming ability which is water-insoluble is one or more water-insoluble polymers selected from the group consisting of a fully saponified polyvinyl alcohol which can be insolubilized after the formation of a coating, a partially saponified polyvinyl alcohol which can be crosslinked by using in combination with a crosslinking agent after the formation of a coating, an oxazoline-modified silicone such as poly(N-propanoylethyleneimine)graft-dimethylsiloxane/γ-aminopropyl methylsiloxane copolymer, polyvinylacetal diethylaminoacetate, Zein (a main component of corn protein), a polyester, polylactic acid (PLA), an acrylic resin (e.g., a polyacrylonitrile resin, a polymethacrylic acid resin), a polystyrene resin, a polyvinyl butyral resin, a polyethylene terephthalate resin, a polybutylene terephthalate resin, a polyurethane resin, a polyamide resin, a polyimide resin, a polyamide-imide resin; more preferably one or more water-insoluble polymers selected from the group consisting of a fully saponified polyvinyl alcohol which can be insolubilized after the formation of a coating, a partially saponified polyvinyl alcohol which can be crosslinked by using in combination with a crosslinking agent after the formation of a coating, a polyvinyl butyral resin, a polyurethane resin, an oxazoline-modified silicone (e.g., poly(N-propanoylethyleneimine)-dimethylsiloxane/γ-aminopropylmethy lsiloxane copolymer), polyvinylacetal diethylaminoacetate and Zein.
<12> The method according to any one of <1> to <11>, wherein the content of component (a) in the composition is preferably 50 mass % or more, more preferably 55 mass % or more, even more preferably 60 mass % or more; preferably 98 mass % or less, more preferably 96 mass % or less, even more preferably 94 mass % or less; the content of component (a) in the composition is preferably 50 mass % or more and 98 mass % or less, more preferably 55 mass % or more and 96 mass % or less, and even more preferably 60 mass % or more and 94 mass % or less.
<13> The method according to any one of <1> to <12>, wherein content of component (b) in the composition is preferably 2 mass % or more, more preferably 4 mass % or more, further more preferably 6 mass % or more; preferably 50 mass % or less, more preferably 45 mass % or less, even more preferably 40 mass % or less; preferably 2 mass % or more and 50 mass % or less, more preferably 4 mass % or more and 45 mass % or less, and even more preferably 6 mass % or more and 40 mass % or less.
<14> The method according to any one of <1> to <13>, wherein the UV protective agent is one or more selected from the group consisting of a benzoic acid-based UV absorber, an anthranilic acid-based UV absorber, a salicylic acid-based UV absorber, a cinnamic acid-based UV absorber, a benzophenone-based UV absorber, and a triazine-based UV absorber.
<15> The method according to <14>, wherein the benzoic acid-based UV absorber is selected from the group consisting of para-aminobenzoic acid (hereafter abbreviated as PABA), glyceryl PABA, ethyldihydroxypropyl PABA, N-ethoxylate PABA ethyl ester, N-dimethyl PABA ethyl ester, N-dimethyl PABA butyl ester, N-dimethyl PABA amyl ester, octyl dimethyl PABA and hexyl diethylaminohydroxybenzoyl benzoate; the anthranilic acid-based UV absorber is homomenthyl-N-acetyl anthranilate; the salicylate-based UV absorber is selected from the group consisting of amyl-salicylate, menthyl salicylate, homomenthyl salicylate, octyl salicylate, phenyl salicylate, benzyl salicylate, and p-isopropanol phenyl salicylate; a cinnamic acid-based UV absorber is selected from the group consisting of ethyl-4-isopropyl cinnamate, ethyl-2,4-diisopropylcinnamate, methyl-2,4-diisopropylcinnamate, propyl-p-methoxycinnamate, isopropyl-p-methoxycinnamate, isoamyl-p-methoxycinnamate, 2-ethylhexyl-p-methoxycinnamate, 2-ethoxyethyl-p-methoxycinnamate, cyclohexyl-p-methoxycinnamate, ethyl-α-cyano-β-phenylcinnamate, 2-ethylhexyl-α-cyano-β-phenylcinnamate, and glyceryl mono-2-ethylhexanoyl di-p-methoxycinnamate; a benzophenone-based UV absorber is selected from the group consisting of 2,4-dihydroxybenzophenone, 2,2'-dihydroxy-4-methoxybenzophenone, 2,2'-dihydroxy-4,4'-dihydroxybenzophenone, 2-hydroxy-4-methoxybenzophenone, 2-hydroxy-4-methoxy-4'-methylbenzophenone, 2-hydroxy-4-methoxybenzophenone, 4-phenylbenzophenone, 2-ethylhexyl-4'-phenylbenzophenone-2-carboxylate, 2-hydroxy-4-n-octoxybenzophenone, and 4-hydroxy-3-carboxybezofenone; a triazine-based UV absorber is selected from the group consisting of 2,4,6-tris [4-(2-ethylhexyoxycarbonyl)anilino]-1,3,5-triazine, 2,4-bis-[{4-(2-ethylhexyloxy)-2-hydroxy}-phenyl]-6-(4-methoxypheny 1)-1,3,5-triazine; and one or more selected from the group consisting of 3-(4'-methylbenzylidene)-dl-camphor, 3-benzylidene-dl-camphor, ethyl urocanate, 2-phenyl-5-methylbenzoxazole, 2,2'-hydroxy-5-methylphenylbenzotriazole, 2-(2'-hydroxy-5-t-octylphenyl)benzotriazole, dibenzarazine, dianisoylmethane, 4-methoxy-4'-t-butyldibenzoylmethane, 5-(3,3-dimethyl-2-norbonylidene)-3-pentane-2-one, a benzene bis-1,3-diketone derivative, and a benzoylpinacolone derivative.

<16> The method according to any one of <1> to <15>, wherein the content of the UV protective agent in the UV composition is preferably 0.1 mass % or more, more preferably 1 mass % or more, further more preferably 5 mass % or more, even more preferably 10 mass % or more; preferably 30 mass % or less, more preferably 25 mass % or less, further preferably 20 mass % or less, and even more preferably 18 mass % or less.

<17> The method according to any one of <1> to <16>, wherein the viscosity of the UV composition at 25° C. is about 100,000 mPa·s or less, preferably 30,000 mPa·s or less, more preferably about 10,000 mPa·s or less.

<18> The method according to any one of <4> to <17>, wherein the oil in a liquid state at 25° C. in the UV composition is selected from the group consisting of a linear or branched hydrocarbon oil such as liquid paraffin, light isoparaffin, liquid isoparaffin, and squalane; a vegetable oil such as a jojoba oil and an olive oil; an animal oil such as liquid lanolin; an ester oil such as a monoalcohol fatty acid ester and a polyvalent alcohol fatty acid ester; a silicone oil such as dimethylpolysiloxane, dimethylcyclopolysiloxane, methylphenylpolysiloxane, methylhydropolysiloxane, and a higher alcohol modified organopolysiloxane; and among them, preferably a hydrocarbon oil, an ester oil, a vegetable oil containing triglyceride, a polar oil such as a silicone oil, preferably one or more selected from the group consisting of a hydrocarbon oil, an ester oil and a silicone oil.

<19> The method according to <18>, wherein the hydrocarbon oil is one or more selected from the group consisting of liquid paraffin, squalane, squalene, n-octane, n-heptane, cyclohexane, light isoparaffin, and liquid isoparaffin, and more preferably one or more selected from the group consisting of liquid paraffin and squalane.

<20> The method according to <18>, wherein the ester oil includes an ester composed of a straight or branched chain fatty acid, and a straight or branched chain alcohol or a polyvalent alcohol, and examples of the ester oil specifically include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethyleneglycol di(2-ethylhexanoate), dipentaerythritol fatty acid ester, N-alkylglycol monoisostearate, neopentylglycol dicaprate, diisostearyl malate, glyceryl di(2-heptylundecanoate), trimethylolpropane tri(2-ethylhexanoate), trimethylolpropane triisostearate, pentaerythritol tetra(2-ethylhexanoate), glyceryl tri(2-ethylhexanoate), trimethylolpropane triisostearate, cetyl 2-ethylhexanoate, 2-ethylhexyl palmitate, diethylhexyl naphthalenedicarboxylate, (C12-15)alkyl benzoate, cetearyl isononanoate, caprylic/capric triglyceride, dicaprylic/capric butyleneglycol, glyceryl trilaurate, glyceryltrimyristate, glyceryltripalmitate, glyceryltriisostearate, glyceryl tri(2-heptylundecanoate), glyceryl tribehenate, glyceryl tricocoate, castor oil fatty acid methyl ester, oleyl oleate, 2-heptylundecyl palmitate, diisobutyl adipate, N-lauryol-L-glutamate-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, di(2-ethylhexyl) succinate, triethyl citrate, 2-ethylhexyl para-methoxycinnamate, and tripropylene glycol dipivalate.

<21> The method according to <18>, wherein the triglyceride is preferably a fatty acid triglyceride, and is one or more selected from the group consisting of an olive oil, a jojoba oil, a macademia nut oil, a medform oil, a castor oil, a safflower oil, a sunflower oil, an avocado oil, a canola oil, a ginseng oil, a rice germ oil, and a rice bran oil.

<22> The method according to <18>, wherein the silicone oil is one or more selected from the group consisting of dimethylpolysiloxane, methylcyclopolysiloxane, methylphenylpolysiloxane, methylhydrogenpolysiloxane, and a higher alcohol modified organopolysiloxane.

<23> The method according to any one of <4> to <22>, wherein the content of the liquid oil in the UV composition is preferably 0.1 mass % or more, more preferably 0.5 mass % or more, and more preferably 5 mass % or more, the content of the liquid oil is preferably 90 mass % or less, and the content of the liquid oil is preferably 0.1 mass % or more and 90 mass % or less, more preferably 0.5 mass % or more and 70 mass % or less, and more preferably 50 mass % or less.

<24> The method according to any one of <3> to <23>, wherein the amount after the application of the UV composition to the skin by a method other than electrostatic spraying is such that the basis weight of the composition is preferably 1 g/m$^2$ or more, more preferably 3 g/m$^2$ or more, even more preferably 5 g/m$^2$ or more, even more preferably 10 g/m$^2$ or more, preferably 85 g/m$^2$ or less, more preferably 60 g/m$^2$ or less, even more preferably 40 g/m$^2$ or less, even more preferably 35 g/m$^2$ or less, preferably 1 g/m$^2$ or more or 85 g/m$^2$ or less, more preferably 3 g/m$^2$ or more or 60 g/m$^2$ or less, even more preferably 60 g/m$^2$ or more or 40 g/m$^2$ or more, and even more preferably 10 g/m$^2$ or more or 35 g/m$^2$ or less, and the amount of the composition applied to the skin or to the coating is preferably 5 g/m², more preferably 10 g/m² or more, even more preferably 15 g/m² or more; preferably 50 g/m² or less, and more preferably 45 g/m² or less.

<25> The method according to any one of <1> to <24>, wherein the electrostatic spraying is performed by using an electrostatic spraying device, the electrostatic spraying device comprises a nozzle, the nozzle is made of a conductive material such as metal or a non-conductive material such as plastic, rubber, and ceramic, and has a shape capable of discharging the composition from the tip thereof.

<26> The method according to any one of <1> to <25>, wherein the electrostatic spraying is performed by using an electrostatic spraying device, the electrostatic spraying device comprises a nozzle and a housing, the nozzle is disposed at one longitudinal end of the housing, and the nozzle is disposed on the housing such that the blowing direction of the composition coincides with the longitudinal direction of the housing and is convex toward the skin side.

<27> The method according to any one of <1> to <25>, which forms a fiber by stretching and deforming the sprayed composition by an electric potential difference, while volatilizing a volatile substance (a solvent), from a droplet to solidify the polymer (a solute having a film-forming ability).

<28> The method according to any of <1> to <27>, wherein the electrostatic spraying is performed by using an electrostatic spraying device, the electrostatic spraying device comprises a nozzle, and the distance between the nozzle and the skin is 50 mm or more and 150 mm or less.

<29> The method according to any one of <1> to <28>, wherein the basis weight of the coating formed by the electrostatic spraying is preferably 0.1 g/m² or more, more preferably 1 g/m² or more, more preferably 3 g/m² or more, preferably 25 g/m² or less, more preferably 15 g/m² or less, even more preferably 10 g/m² or less, preferably 0.1 g/m² or more and 25 g/m² or less, more preferably 1 g/m² or more and 15 g/m² or less, even more preferably 3 g/m² or more and 10 g/m² or less, and the amount of the spray composition used is preferably 1 g/m$^{-2}$ or more, more preferably 3 g/m$^{-2}$ or more, even more preferably 5 g/m$^{-2}$ or more, even more preferably 25 g/m$^{-2}$ or less, more preferably 15 g/m$^{-2}$ or less, even more preferably 10 g/m$^{-2}$ or less.

<30> The method for producing a coating according to any one of <1> to <29>, wherein component (a) is a volatile substance containing at least ethanol, and component (b) is one or more selected from the group consisting of a polyvinyl butyral resin and a polyurethane resin.

<31> The method for producing a coating according to any one of <1> to <30>, wherein the content of component (a) in the composition containing a UV protective agent is 30 mass % or more, preferably 55 mass % or more, more preferably 60 mass % or more; 98 mass % or less, preferably 96 mass % or less, even more preferably 94 mass % or less; 30 mass % or more and 98 mass % or less, preferably 55 mass % or more and 96 mass % or less, even more preferably 60 mass % or more and 94 mass % or less.

<32> The method for producing a coating according to any one of <1> to <31>, wherein the content of component (b) in the composition containing a UV protective agent is 2 mass % or more, preferably 4 mass % or more, more preferably 6 mass % or more; 30 mass % or less, preferably 45 mass % or less, even more preferably 40 mass % or less; 2 mass % or more and 50 mass % or less, preferably 4 mass % or more and 45 mass % or less, and even more preferably 6 mass % or more and 40 mass % or less.

<33> The method according to any one of <1> to <32>, wherein the content of component (a) is 30 mass % or more and 98 mass % or less in the composition, and the content of component (b) is 2 mass % or more and 50 mass % or less in the spraying composition.

<34> The method according to any one of <1> to <32>, wherein the content of component (a) is 55 mass % or more and 96 mass % or less in the composition, and the content of component (b) is 4 mass % or more and 45 mass % or less in the spraying composition.

<35> The method according to any one of <1> to <32>, wherein the content of component (a) is 60 mass % or more and 94 mass % or less in the composition, and the content of component (b) is 6 mass % or more and 40 mass % or less in the spraying composition.

<36> The method according to any one of <1> to <35>, wherein component (a) is a volatile substance containing at least ethanol, and component (b) is one or more selected from the group consisting of a polyvinyl butyral resin and a polyurethane resin.

EXAMPLES

The present invention will be explained in more detail by means of the following examples. However, the scope of the present invention is not limited to these examples. Unless otherwise specified, "%" means "mass %".

Test Example 1

Example 1

(1) Preparation of Spraying Composition A

As component (a) of the spraying composition, 99.5% ethanol (manufactured by Wako Pure Chemical Industries, Ltd.) was used. Polyvinyl butyral (manufactured by Sekisui Chemical Co., Ltd.: trade name S-LEC B) was used as component (b).

Component (a), component (b), and additive (Eldew PS-203 manufactured by Ajinomoto Healthy Supply Co., Ltd.) were weighed into a 1 L glass-made beaker, and stirred at room temperature for about 12 hours using a propeller mixer to obtain uniformly transparent solutions. This was used as the spraying composition (A).

The content of component (a), component (b) and additives were 80 parts by mass, 14 parts by mass and 6.0 parts by weight, respectively.

(2) Application of UV Compositions

Cosmetic A shown in Table 1 below was used as the UV composition. The UV composition was applied to the back of the human hand. The basis weight of the applied cosmetic was 11.5 g/m$^{-2}$.

TABLE 1

Cosmetic A

| Component | | Content (mass %) |
|---|---|---|
| 2-ethylhexyl-p-methoxycinnamate | Ubinul MC80 | 10 |
| Hexyl diethylaminohydroxybenzoyl benzoate | Ubinul A plus Granular | 1 |
| 2,4-Bis-[{4-(2-ethylhexyloxy)-2-hydroxy}-phenyl]-6-(4-methoxyphenyl)-1,3,5-triazine | Ubinul T-150 | 1 |
| 2,4,6-Tris[4-(2-ethylhexyloxycarbonyl)anilino]-1,3,5-triazine | Tinosorb S | 2 |
| (C12-C15) alkyl benzoate | Finsolv TN | 3 |
| Methylpolysiloxane | Silicone KF-96A-10CS | 1 |
| Acrylic acid/alkyl methacrylate copolymer | Pemulen TR-1 | 0.25 |
| Acrylic acid/alkyl methacrylate copolymer | Pemulen TR-2 | 0.1 |
| 2-amino-2-methylpropanol | AMP | 0.1 |
| Polyoxyethylene 2-hexyldecyl ether | Emulgen 1620G | 0.1 |
| Purified Water | Purified Water | Balance |
| | | 100 |

(3) Step of Electrostatic Spraying

An electrostatic spraying device having the configuration shown in FIG. 1 and having the appearance shown in FIG. 2 was used, and an electrostatic spraying was performed for 30 seconds toward a site on which cosmetic had been applied. The conditions of the electrostatic spraying are as follows.

Applied voltage: 10 kV
Distance between conductive nozzle and skin: 100 mm
Volume of spray composition: 5 mL/h
Environment: 25° C., 40% RH The electrostatic spray formed a porous coating of a fiber deposit across the site where a cosmetic was applied. The coating was a circle approximately 4 cm in diameter and the mass was approximately 7 mg. The basis weight was approximately 6 g·m$^{-2}$.

Examples 2 to 9, Comparative Examples 1 to 4

A coating was formed in the same manner as in Example 1 except that the basis weight was changed to that shown in Table 2.

TABLE 2

| | UV composition | | Spraying composition | | Basis weight ratio | |
|---|---|---|---|---|---|---|
| | type | Basis weight g/m$^{-2}$ | type | Basis weight g/m$^{-2}$ | Spraying composition/ UV composition | Order of coating |
| Example 1 | Cosmetic A | 11.5 | Composition A | 6 | 0.52 | UV composition -> spraying composition |
| Example 2 | Cosmetic A | 11.5 | Composition A | 12 | 1.04 | UV composition -> spraying composition |
| Example 3 | Cosmetic A | 11.5 | Composition A | 24 | 2.09 | UV composition -> spraying composition |
| Example 4 | Cosmetic A | 5.7 | Composition A | 6 | 1.05 | UV composition -> spraying composition |
| Example 5 | Cosmetic A | 5.7 | Composition A | 12 | 2.11 | UV composition -> spraying composition |
| Example 6 | Cosmetic A | 81.7 | Composition A | 6 | 0.07 | UV composition -> spraying composition |
| Example 7 | Cosmetic A | 81.7 | Composition A | 12 | 0.15 | UV composition -> spraying composition |
| Example 8 | Cosmetic A | 81.7 | Composition A | 24 | 0.29 | UV composition -> spraying composition |
| Example 9 | Cosmetic A | 11.5 | Composition A | 6 | 0.52 | Spraying composition -> UV composition |
| Comparative Example 1 | Cosmetic A | 11.5 | — | 0 | 0 | UV composition -> spraying composition |
| Comparative Example 2 | Cosmetic A | 5.7 | — | 0 | 0 | UV composition -> spraying composition |
| Comparative Example 3 | Cosmetic A | 81.7 | — | 0 | 0 | Spraying composition -> UV composition |
| Comparative Example 4 | — | 0 | Composition A | 6 | — | UV composition -> spraying composition |

Comparative Example 5

The coating was formed in the same manner as in Example 1 except that the same composition as in Example 1 was directly applied without electrostatic spraying.

(4) Evaluation

[SPF]

In order to compare the UV protective performance of the obtained coating, an SPF test was conducted. Five sprayed coatings were measured on substrates (HD-6 manufactured by Labsphere, Inc.) and the mean was used as SPFs. SPF analyzers (UV-2000S manufactured by Labsphere) were used for measurements. The displayed SPF of 50 or more was designated as (a), the displayed SPF of 20 or more and less than 50 was designated as (b), and the displayed SPF of less than 20 was designated as (c).

[Durability]

The SPF before and after 10 rubs of the coating with the finger was measured and used as an index of the durability of the coating. When the SPF was maintained at 80% or more after 10 times as compared with the first SPF, the SPF was designated as (a), the SPF maintained at 60% or more and less than 80% was designated as (b), and the SPF maintained at less than 60% was designated as (c).

[Coating Feel]

The feeling of discomfort when the coating was formed on the back of the hand was determined by sensory evaluation. Those that did not feel discomfort were designated as (a), those that were somewhat annoying were designated as (b), and those that were very annoying were designated as (c).

[Appearance]

The appearance when the coating was deposited on the back of the hand was determined by sensory evaluation. Those who felt a sense of integration with the back of the hand were designated as (a), those who felt a slight sense of integration were designated as (b), and those who felt a scarce sense of integration were designated as (c).

The results are shown in Table 3.

TABLE 3

|  | SPF | Durability | Coating feel | Appearance |
| --- | --- | --- | --- | --- |
| Example 1 | b | a | a | a |
| Example 2 | a | a | a | a |
| Example 3 | a | a | b | b |
| Example 4 | b | a | a | a |
| Example 5 | b | a | a | a |
| Example 6 | a | a | b | a |
| Example 7 | a | a | a | a |
| Example 8 | a | a | a | b |
| Example 9 | a | a | a | a |
| Comparative Example 1 | c | b | a | a |
| Comparative Example 2 | c | b | a | a |
| Comparative Example 3 | c | b | a | a |
| Comparative Example 4 | c | b | a | a |

Examples 10 to 13

Using Composition A, Composition B, or Composition C in Tables 4 to 6 as the spraying composition, and using Cosmetic A described hereinbefore, Cosmetic B or Cosmetic C of Tables 7 to 8 as the UV composition, application of UV Composition and electrostatic spraying were carried out in the same manner as in Example 2, and evaluation was carried out in the same manner as in Example 2. The results are shown in Tables 9 and 10.

Examples 14

Coatings prepared by electrostatically spraying the spraying composition A of Table 4 onto another substrate in advance were evaluated in the same manner as in Example 2 by applying the cosmetic A and patching the coating from above the substrate. The results are shown in Tables 9 and 10.

TABLE 4

| Composition A | | |
| --- | --- | --- |
| | | Content (%) |
| Component (a) | Ethanol | 80 |
| Component (b) | Polyvinyl butyral | 14 |
| Other | Di(phytosteryl/octyldodecyl) lauroyl glutamate*[1] | 6 |

*[1]Eldew PS-203 (manufactured by Ajinomoto Co., Inc.)

TABLE 5

| Composition B | | |
| --- | --- | --- |
| | | Content (%) |
| Component (a) | Ethanol | 52 |
| Component (a) | 1-butanol | 26 |
| Component (b) | polyacrylate*[1] | 22 |

*[1]Dermacryl79 (manufactured by AkzoNobel)

TABLE 6

| Composition C | | |
| --- | --- | --- |
| | | Content (%) |
| Component (a) | Ethanol | 80 |
| Component (b) | Polyvinyl acetal diethylaminoacetate *[2] | 14 |
| Other | Di(phytosteryl/octyldodecyl) lauroyl glutamate *[1] | 6 |

*[1] Eldew PS-203 (manufactured by Ajinomoto Co., Inc.)
*[2] AEA (manufactured by Mitsubishi Chemical Foods Corporation)

TABLE 7

Cosmetic B

| Component | | Content (%) |
|---|---|---|
| 2-ethylhexyl-p-methoxycinnamate | Uvinul MC80 manufactured by BASF | 5 |
| (C12~15) alkyl benzoate | Innospec Active Finsolv TNs, manufactured by Chemicals LLC | 5 |
| Siliconized zinc oxide | MZ-504R3M made by Tayca Corporation (Particle size: 25 nm) | 10 |
| Polyoxyethylene/methylpolysiloxane copolymer | Silicone SH3775M manufactured by Toray Dow Corning | 0.8 |
| Methylcyclopolysiloxane | Silicone TSF405A manufactured by Momentive Performance Materials Japan, Inc. | 40 |
| Ethanol | | 10 |
| Purified Water | | Balance |
| | | 100 |

TABLE 8

Cosmetic C

| Component | | Content (%) |
|---|---|---|
| 2-ethylhexyl-p-methoxycinnamate | Ubinul MC80 manufactured by BASF | 10 |
| (C12-15) alkyl benzoate | Finsolv TNs, made of Innospec Active Chemicals LLC | 10 |
| Sodium acrylate/sodium acryloyldimethyltaurate copolymer | SIMULGEL EG manufactured by SEP PIC, Inc. | 1.5 |
| Sorbitan monostearate | Rheodol SP-S10V, manufactured by Kao Corporation | 0.7 |
| Polyoxyethylene sorbitan monostearate | Rheodol SP-S10V Rheodol TW-S120 manufactured by Kao Corporation | 0.5 |
| Silicone-treated zinc oxide | MZ-504R3M (particle size: 25 nm) manufactured by Tayca | 10 |
| Ethanol | | 10 |
| Purified Water | | Balance |

TABLE 9

| | UV composition | | Spraying composition | | Basis weight ratio | |
|---|---|---|---|---|---|---|
| | type | Basis weight g/m$^{-2}$ | Spraying composition | Basis weight g/m$^{-2}$ | Spraying composition/ UV composition | Order of coating |
| Example 10 | Cosmetic A | 11.5 | Composition B | 6 | 0.52 | UV composition -> spraying composition |
| Example 11 | Cosmetic A | 11.5 | Composition C | 6 | 0.52 | UV composition -> spraying composition |
| Example 12 | Cosmetic B | 11.5 | Composition A | 6 | 0.52 | UV composition -> spraying composition |
| Example 13 | Cosmetic C | 11.5 | composition A | 6 | 0.52 | UV composition -> spraying composition |
| Example 14 | Cosmetic A | 11.5 | Composition A | 6 | 0.52 | UV composition -> spraying composition |

TABLE 10

| | SPF | Durability | Coating feel | Appearance |
|---|---|---|---|---|
| Example 10 | a | a | a | a |
| Example 11 | a | a | a | a |
| Example 12 | a | a | a | a |
| Example 13 | a | a | a | a |
| Example 14 | a | b | b | a |

From Tables 3, 9 and 10, it can be seen that the SPF was dramatically improved by the method of the present invention, and the durability of the SPF values was also excellent. Further, there was no discomfort in the coating feel, and the appearance was excellent. It is conceivable that the effect of the present invention in improving SPFs is based not only on the presence of UV absorbers on the skin, but also on the uniform distribution of the UV absorbers on the coating and on uniform presence of the UV absorbers on the skin.

EXPLANATION OF SYMBOLS

10 Electrostatic spraying device
11 Low-voltage power supply
12 High-voltage power supply
13 Auxiliary electrical circuit
14 Microgear pump
15 Container
16 Nozzle
17 Pipe
18 Flexible pipe
19 Current limiting resistor
20 Housing

The invention claimed is:

1. A method for forming a UV protective porous coating in the form of a deposit of continuous fibers on skin, the method comprising:
   applying a first composition comprising a UV protective agent to the skin, and
   separately from the applying the first composition, electrostatically spraying a second composition comprising a component (a) and a component (b) directly onto the skin, thereby depositing the second composition in the form of a deposit of continuous fibers at a site of application to form the UV protective porous coating on the skin,
   wherein
   the component (a) is a volatile substance comprising at least one member selected from the group consisting of ethanol and 1-butanol, wherein a content of the component (a) in the second composition is from 30 mass % to 98 mass %,
   the component (b) comprises at least one member selected from the group consisting of polyvinyl butyral, polyacrylate and polyvinyl acetal diethylaminoacetate, wherein a content of the component (b) in the second composition is from 2 mass % to 50 mass %,
   wherein the UV protective porous coating comprises a deposit comprising continuous fibers, and the continuous fibers are formed from the water-insoluble polymer by the electrostatically spraying,
   wherein the continuous fibers are formed from the water-insoluble polymer during the electrostatically spraying of the second composition,
   wherein the second composition for the electrostatically spraying is in a liquid form at 20° C. and
   wherein a content ratio of the component (a) and the component (b), ((a)/(b)), is from 0.5 to 40.

2. The method according to claim 1, wherein the applying the first composition comprising the UV protective agent to the skin is performed by a method other than an electrostatic spraying.

3. The method according to claim 1, wherein the UV protective agent is a UV absorber.

4. The method according to claim 1, wherein the electrostatic spraying is performed using an electrostatic spraying device comprising a container comprising the second composition, a nozzle for discharging the second composition, a supply device for supplying the second composition comprised in the container to the nozzle, and a power supply for applying a voltage to the nozzle.

5. The method according to claim 1, wherein the component (a) is a volatile substance comprising 1-butanol.

6. The method according to claim 1, wherein the component (a) is a volatile substance comprising ethanol.

7. The method according to claim 1, wherein the component (a) is a volatile substance comprising ethanol, and a content of the ethanol in the volatile substance is from 50 mass % to 100 mass %.

8. The method according to claim 6, wherein the content ratio of (a) ethanol to the component (h), ((a)/(b)), is from 0.5 to 40.

9. The method according to claim 1, wherein the content of the component (a) in the second composition is from 55 mass % to 96 mass %, and the content of the component (b) in the second composition is from 4 mass % to 45 mass %.

10. The method according to claim 1, wherein the content of the component (a) in the second composition is from 60 mass % to 94 mass %, and the content of the component (h) in the second composition is from 6 as % to 40 mass %.

11. The method according to claim 1, wherein the component (a) is a volatile substance comprising ethanol, and the component (b) comprises polyvinyl.

12. The method according to claim 1, wherein the content of the component) in the second composition is from 6 mass % to 40 mass %.

13. The method according to claim 1, wherein the fiber has a length which is at least 100 times greater than a thickness of the fiber.

14. The method according to claim 1, wherein the second composition is electrostatically sprayed through a nozzle which comprises a minute space through which the spray composition flows and that extends in the longitudinal direction of the nozzle,
   wherein a diameter of the cross section of the minute space is from 100 μm to 1,000 μm, and
   wherein the second composition for electrostatic spraying is in a liquid form after passing through the nozzle and before passing through the nozzle.

* * * * *